US009005623B2

(12) United States Patent
Moste et al.

(10) Patent No.: US 9,005,623 B2
(45) Date of Patent: Apr. 14, 2015

(54) FLU VIRUS HEMAGGLUTININ SPECIFIC MONOCLONAL ANTIBODIES

(75) Inventors: Catherine Moste, Charbonnieres les Bains (FR); Isabelle Legastelois, Saint Andeol le Chateau (FR); Michel Chevalier, Beaurepaire (FR); Laurent Thion, Bourg de Thizy (FR)

(73) Assignee: Sanofi Pasteur, SA, Lyons (FR)

( * ) Notice: Subject to any disclaimer, the term of this patent is extended or adjusted under 35 U.S.C. 154(b) by 638 days.

(21) Appl. No.: 12/246,803

(22) Filed: Oct. 7, 2008

(65) Prior Publication Data

US 2009/0092620 A1 Apr. 9, 2009

Related U.S. Application Data

(60) Provisional application No. 61/063,658, filed on Feb. 4, 2008.

(30) Foreign Application Priority Data

Oct. 8, 2007 (FR) ..................................... 07 58134

(51) Int. Cl.
| | |
|---|---|
| *A61K 39/42* | (2006.01) |
| *A61K 39/145* | (2006.01) |
| *A61K 39/21* | (2006.01) |
| *G01N 33/53* | (2006.01) |
| *C07K 16/10* | (2006.01) |
| *A61K 31/737* | (2006.01) |
| *G01N 33/569* | (2006.01) |

(52) U.S. Cl.
CPC ............ *C07K 16/1018* (2013.01); *A61K 31/737* (2013.01); *C12N 2760/16111* (2013.01); *G01N 33/56983* (2013.01); *G01N 2333/11* (2013.01); *G01N 2469/10* (2013.01)

(58) Field of Classification Search
USPC ......................................................... 424/147
See application file for complete search history.

(56) References Cited

U.S. PATENT DOCUMENTS

| | | | |
|---|---|---|---|
| 4,625,015 | A | 11/1986 | Green et al. |
| 5,589,174 | A | 12/1996 | Okuno et al. |

OTHER PUBLICATIONS

Schulze IT. Effects of Glycosylation on the Properties and Functions of Influenza Virus Hemagglutinin. The Journal of Infectious Diseases 1997;176 (Suppl 1):S24-8.*
Gamblin, et al. The Structure and Receptor Binding Properties of the 1918 Influenza HemagglutininScience. 2004; 303: 1838-1842.*
Manzi and Halbeek. Chapter 2, Saccharide Structure and Nomenclature. Varki A, Cummings R, Esko J, et al., editors. Essentials of Glycobiology. Cold Spring Harbor (NY): Cold Spring Harbor Laboratory Press; 1999.*
Gerentes et al.: "A Sensitive and Specific ELISA Immunocapture Assay for Rapid Quantitation of Influenza A/H3N2 Neuraminidase Protein," Journal of Virological Methods, 73, pp. 185-195 (1998).
Aytay et al.: "Single Amino Acid Substitutions in the Hemagglutinin Can Alter the Host Range and Receptor Binding Properties of H1 Strains of Influenza A Virus," Journal of Virology, vol. 65, No. 6 pp. 3022-3028 (1991).
Karaivanova et al.: "Sulphation of N-linked Oligosaccharides of Vesicular Stomatitis and Influenza Virus Envelope Glycoproteins: Host Cell Specificity, Subcellular Localization and Identification of Substituted Saccharides," Biochem. J., 329, pp. 511-518 (1998).
Okuno et al.: "A Common Neutralizing Epitope Conserved Between the Hemagglutinins of Influenza A Virus H1 and H2 Strains," Journal of Virology, vol. 67, No. 5, pp. 2552-2558 (1993).
Nakagawa et al.: "Antigenic Variants with Amino Acid Deletions Clarify a Neutralizing Epitope Specific for Influenza B Virus Victoria Group Strains," Journal of General Virology, 82, pp. 2169-2172 (2001).
Nakagawa et al.: "Rapid Detection and Identification of Two Lineages of Influenza B Strains with Monoclonal Antibodies," Journal of Virological Methods, 79, pp. 113-120 (1999).
Nakagawa et al.: "Characterization of New Epidemic Strains of Influenza B Virus by Using Neutralizing Monoclonal Antibodies," Journal of Medical Virology, 65, pp. 745-750 (2001).
Mir-Shekari et al.: "The Glycosylation of the Influenza A Virus Hemagglutinin by Mammalian Cells," The Journal of Biological Chemistry, vol. 272, No. 7, pp. 4027-4036 (1997).
Bianchi et al.: "Universal Influenza B Vaccine Based on the Maturational Cleavage Site of the Hemagglutinin Precursor," Journal of Virology, vol. 79, No. 12, pp. 7380-7388 (2005).

* cited by examiner

*Primary Examiner* — Stacy B Chen
*Assistant Examiner* — Barry A Chestnut
(74) *Attorney, Agent, or Firm* — McNeill Baur PLLC

(57) ABSTRACT

The invention relates to a flu virus hemagglutinin-specific monoclonal antibody which recognizes an antigenic structure present both on the H1 and H3 subtypes of the hemagglutinins of type A flu viruses and on the hemagglutinin of type B flu viruses. Within type B flu viruses, the antigenic structure is present on the hemagglutinins of type B flu viruses belonging to the B/Victoria group and/or to the B/Yagamata group.

14 Claims, 3 Drawing Sheets

■ = N-acetylglucosamine

△ = fucose

○ = mannose

● ◆ = galactose sulfate

FLU VIRUS HEMAGGLUTININ SPECIFIC MONOCLONAL ANTIBODIES

CROSS-REFERENCE TO RELATED APPLICATIONS

This application claims the benefit of priority of U.S. provisional application 61/063,658, filed Feb. 4, 2008.

BACKGROUND OF THE INVENTION

1. Field of the Invention

The invention relates to a monoclonal antibody which recognizes a glycosylated antigenic structure present on the hemagglutinin of both the type A flu virus and the type B flu virus, and also to the use thereof for diagnostic, therapeutic, and purification purposes.

2. Summary of the Related Art

There are 3 types of flu virus (types A, B and C) responsible for infectious pathologies in humans and animals. Currently, the type A and type B viruses are the agents responsible for the flu epidemics and pandemics observed in humans.

The type A viruses circulating mainly in humans and birds are subdivided into subtypes according to the antigenic structure of hemagglutinin (HA) and of neuraminidase (NA), which are the main constituents of the viral envelope. 16 HA subtypes (H1 to H16) and 9 NA subtypes (N1 to N9) have been identified. The subtype of a type A virus is defined by the HA subtype and the NA subtype that it carries. The H1N1 and H3N2 virus subtypes are those which currently circulate in humans. It is feared that the H5N1 subtype or the H7N1 subtype which circulate in birds will adapt to humans and be responsible for a new pandemic. It is not out of the question, either, that the H2N2 subtype which circulated between 1957 and 1968 in humans might reappear and also be responsible for a pandemic in individuals below the age of 40.

The type B virus strains are strictly human. The antigenic variations in the HA within the type B strains are weaker than those observed within the type A strains. The type B strains, isolated since the 1970s, are divided into two distinct phylogenetic and antigenic groups according to the genetic sequence of the HA (Lindstrom SE, Journal of Virology, 1999, pp 4413-4426). The B/Victoria/2/87 (B/Victoria) is the leading strain of the first group, while the B/Yamagata/16/88 (B/Yagamata) is the leading strain of the second group. The type B virus strains which were isolated in the 1980s belong especially to the B/Victoria group, whereas the strains which were isolated in the 1990s belong especially to the B/Yamagata group. In 1994, the B/Victoria group reemerged in China and, since then, type B strains belonging to the two groups have been isolated during the same flu season (Nakagawa N et al., Journal of Medical Virology, 2001, pp 745-750).

Flu virus HA is, in its natural form, a trimeric glycoprotein with a molecular weight of approximately 220,000 daltons. It is subjected to a strong "selection pressure" with, as a result, the appearance:

- of major variations in its structure, resulting in an "antigenic shift". These phenomena are observed in the type A viruses and are responsible for the appearance of reassortant viruses having a new HA subtype. These reassortant viruses may be responsible for new pandemics in humans or animals;
- of minor variations in its structure due mainly to point mutations resulting in an "antigenic drift". These phenomena are observed both in type A viruses and in type B viruses. They are responsible for the appearance of new viral strains which can trigger epidemics or sporadic flu foci during inter-pandemic periods.

Flu virus HA also contains numerous glycosylation sites (between 7 and 9 on the H1 and H3 subtypes). The glycosylated chains are linked to the protein structure by means of N-glycosidic linkages which link an asparagine of the protein sequence to an N-acetylglucosamine of the sugar chain. Two types of glycosylated chains are conventionally distinguished according to their sugar composition: type I glycosylated chains contain essentially N-acetylglucosamine, mannose, galactose and fucose, and type II glycosylated chains contain essentially mannose and N-acetylglucosamine. The N-glycosylation of HA is carried out through the dolichol pathway that results in the transfer in block of the oligosaccharide sequence (glucose)$_3$-(mannose)$_9$-(N-acetylglucosamine)$_2$ onto the asparagines which are in a consensus sequence of Asn-X-Ser/Thr type in the protein chain (Virology, 133, 77-91 (1984)). The oligosaccharide sequence transferred in block has a "three-antenna" configuration represented schematically in FIG. 2.

As was shown by Mir-Shekari S. Y. et al. (Journal of Biological Chemistry, 272, 4027-4036 (1997)), the initial three-antenna sequences transferred then individually undergo a transformation process according to their anchoring site on the HA protein chain. The glycosylated structures may finally be two-antenna, three-antenna or four-antenna structures, with a smaller or larger number of sugars on each of the antennae.

In order to prevent flu epidemics, vaccines containing two strains of virus A belonging to different subtypes (currently the H1N1 and H3N2 subtypes) and a type B virus strain are annually prepared. The vaccinal strains used take into account the variations which have occurred from one year to the other at the level of the HA protein sequence and which are responsible for the appearance of new epidemic foci. These new strains are identified and characterized using very precise diagnostic tools, in particular by means of monoclonal antibodies which reveal very specifically the variations observed. These monoclonal antibodies have a very narrow specificity since they generally recognize the HA of a single viral strain. They are "strain" specific.

Monoclonal antibodies having a broader specificity (referred to as "subtype" specificity also exist for characterizing type A viruses. They are "subtype" specific insofar as they recognize the HAs of viral strains having the same HA subtype but not the HAs of viral strains of another subtype. Monoclonal antibodies specific for the H1 subtype or for the H3 subtype in particular exist. A cross-reactive monoclonal antibody which recognizes both the HAs of flu viruses belonging to the H1N1 and H2N2 subtypes has been reported in U.S. Pat. No. 5,589,174.

As regards the monoclonal antibodies directed against the HA of type B viruses, N. Nakagawa has described a battery of monoclonal antibodies directed against the HA of strains belonging to the two groups B/Victoria and B/Yagamata. The monoclonal antibodies 10B8, 8E6, 1H12, 2H12 and 9E10 recognize the HA of type B virus strains belonging to the B/Victoria group which were isolated between 1996 and 1997, but not the HA of type B virus strains isolated during this same period and which belong to the B/Yamagata group (Nakagawa N et al., Journal of Virological methods (1999), 113-120). These monoclonal antibodies were obtained by immunizing mice with the B/Nagasaki/1/87 strain which belongs to the B/Victoria group. Monoclonal antibodies 1B2, 5B1, 5H4, 7H11, 8B3 and 9G6, obtained after immunization of mice with the B/Mie/1/93 strain (which belongs to the B/Yagamata group), which recognize the HA of type B virus strains belonging to the B/Yamagata group, have also been described (Nakagawa N et al., Journal of Medical Virology (2001), 745-750).

SUMMARY OF THE INVENTION

To our knowledge, monoclonal antibodies which recognize both the HA of strains belonging to the B/Victoria group and the HA of strains belonging to the B/Yagamata group have never been described.

Even though the use of monoclonal antibodies having a restricted specificity is found to be extremely valuable for following the antigenic variations of HA which occur regularly within the circulating viral strains, it may also prove to be very useful to have monoclonal antibodies which have a broad spectrum of flu virus recognition. In this way, the presence of a flu virus in a biological material is readily and rapidly detected without it being necessary to use an entire battery of antibodies to reveal it. They may also be used as an alternative to the strain-specific monoclonal antibodies which are normally used to verify flu vaccines when said antibodies are not available within sufficiently short periods of time.

The present invention meets this need and relates to a flu virus hemagglutinin-specific monoclonal antibody which recognizing an antigenic structure that is present both on the H1 and H3 subtypes of the hemagglutinins of type A flu viruses and on the hemagglutinins of type B flu viruses.

All patents, patent applications, and other publications are hereby incorporated by reference.

DETAILED DESCRIPTION OF THE INVENTION

Figure 1:
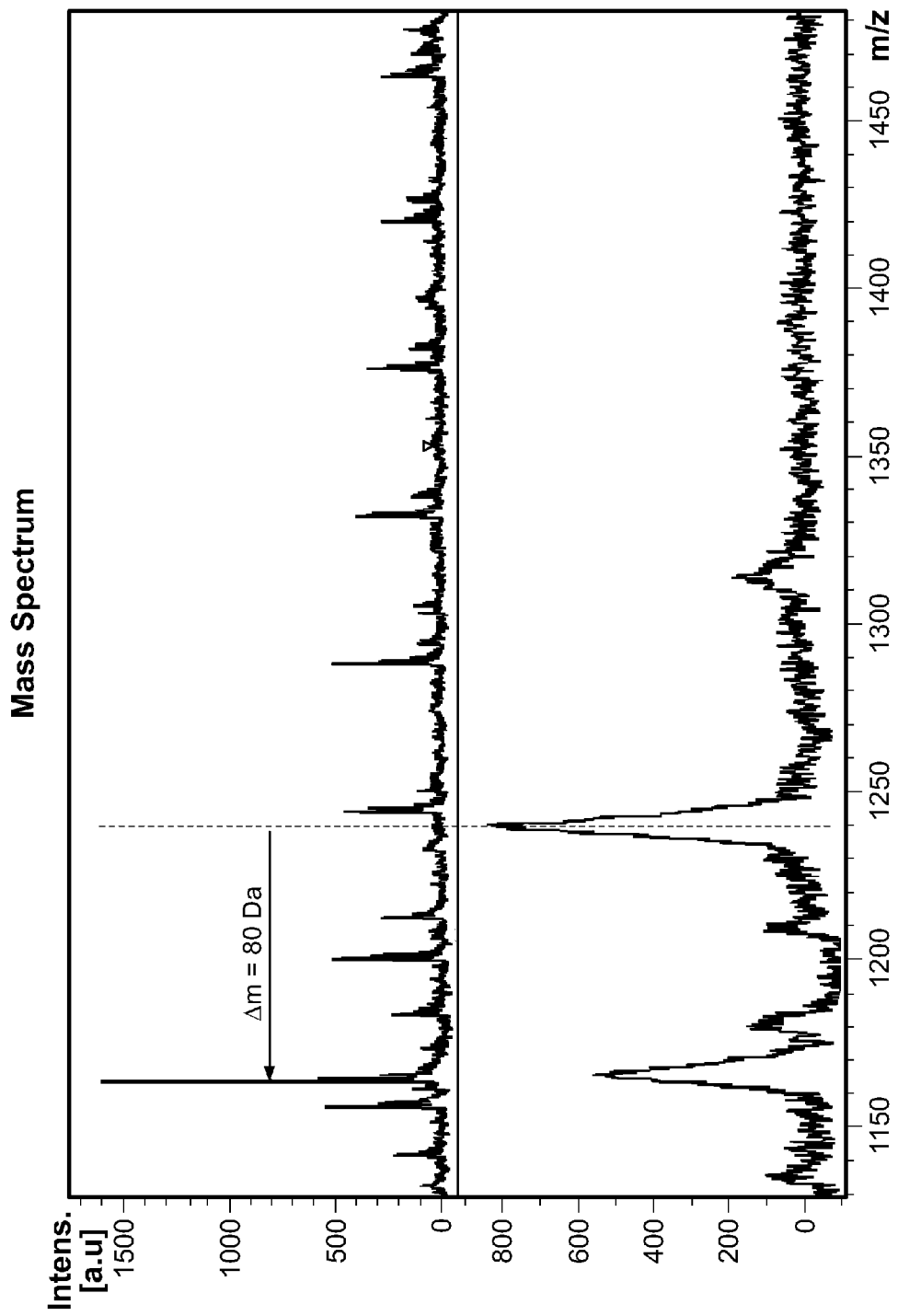
FIG. 1 represents the MALDI-TOF mass spectra of the glycans before (bottom spectrum) and after treatment with aqueous ammonia (top spectrum).
Figure 2:
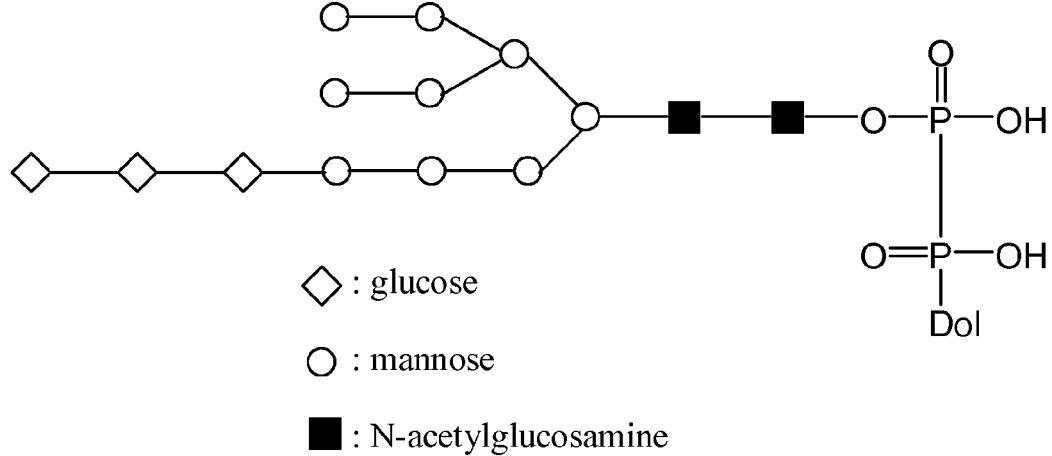
FIG. 2 is a schematic depiction of the "three-antenna" configuration of the oligosaccharide sequence linked to the dolichol pyrophosphate transferred onto the asparagines in a consensus sequence of Asn-X-Ser/Thr type in the protein chain of HA.

The monoclonal antibody according to the invention is specific for flu virus HA since it does not recognize the other components of the flu virus, in particular the NA, the M protein or the NP protein. Furthermore, it inhibits at least the hemagglutinating activity mediated by type A flu virus strains belonging to the same subtype. Its recognition spectrum with respect to flu virus hemagglutinins is, on the other hand, very broad. It is broader than the antibodies which have a "subtype" specificity (specificity limited to an HA subtype of type A viruses) or a "type" specificity (specificity limited to HAs of a single type of virus). Indeed, the monoclonal antibody according to the invention recognizes both the hemagglutinins of type A and B viruses.

With respect to the type A viruses, the monoclonal antibody according to the invention recognizes an antigenic determinant present on the H1 and H3 subtypes. In particular, it recognizes viral strains belonging to the H1N1 subtype, for instance the A/New Calcdonia/20/99 strain and/or the A/Chile/1/83X83 strain, and viral strains belonging to the H3N2 subtype, for instance the A/Panama/2007/99 strain, the A/Wisconsin/67/2005 strain, the A/New York/55/2004 strain, the A/Wyoming/03/2003 strain, the A/Hong Kong/1/68 strain, the A/Beijing/32/92 strain, the A/Shangdong/9/93 strain, the A/Johannesburg/33/94 strain, the A/Nanchang/933/95 strain and/or the A/Sydney/5/97 strain.

With respect to the type B flu viruses, the monoclonal antibody also recognizes an antigenic structure present on the HA of type B viral strains. In particular, it recognizes the B/Shangdong/7/97 strain, the B/Jiangsu/10/03 strain, the B/Brisbane 23/02 strain, the B/Yagamata 16/88 strain, the B/Beijing 1/87 strain and/or the B/Malaysia/2506/04 strain. It generally recognizes both type B virus strains belonging to the B/Victoria group (such as the B/Shangdong/7/97 strain) and type B virus strains belonging to the B/Yagamata group (such as the B/Jiangsu/10/03 strain).

The invention therefore also comprises a flu virus HA-specific monoclonal antibody recognizing an antigenic structure that is present both on the H1 and H3 subtypes of the hemagglutinins of type A flu viruses and on the hemagglutinin of type B flu viruses belonging to the B/Victoria group and/or to the B/Yagamata group.

A monoclonal antibody according to the invention therefore specifically recognizes the HA of at least one type A flu virus strain having the H1N1 subtype, the HA of at least one type A flu virus strain having the H3N2 subtype, the HA of at least one type B flu virus strain belonging to the B/Victoria group and the HA of at least one type B flu virus strain belonging to the B/Yagamata group.

Generally, a monoclonal antibody according to the invention recognizes the HAs of several type A flu virus strains having the H1N1 subtype, the HAs of several type A flu virus strains having the H3N2 subtype, the HAs of several type B flu virus strains belonging to the B/Victoria group and the HAs of several type B flu virus strains belonging to the B/Yagamata group. Viral strains of H1N1 type which are recognized by a monoclonal antibody according to the invention include the A/New Calcdonia/20/99 and A/Chile/1/83/X83 strains. Viral strains of H3N2 type which are recognized by a monoclonal antibody according to the invention include the A/Wyoming/3/03 and A/New York/55/04 strains. Type B viral strains belonging to the B/Victoria group which are recognized by an antibody according to the invention include the B/Shandong/7/97 and B/Brisbane/32/02 strains. Type B viral strains belonging to the B/Yagamata group which are recognized by a monoclonal antibody according to the invention include the B/Yagamata/16/88 and B/Jiangsu/10/03 strains. In particular, the monoclonal antibodies Y6F5 and Y13F9 exhibit these recognition characteristics (cf. example 1.2).

Preferably, a monoclonal antibody according to the invention recognizing an antigenic structure that is present on the HAs of more than two type A flu virus strains having the H1N1 subtype, on the HAs of more than two A flu virus strains having the H3N2 subtype, on the HAs of more than two type B flu virus strains belonging to the B/Victoria group, and on the HAs of more than two type B flu virus strains belonging to the B/Yagamata group.

In particular, a monoclonal antibody according to the invention recognizes viral strains in which the HAs belong to the H5 and/or H7 subtype that might be involved in the development of flu virus pandemic strains. The monoclonal antibody recognizes in particular the A/Vietnam/1194/04 NIBRG14 strain, which is an avian strain of H5N1 subtype accessible from the National Institute for Biological Standards and Controls (NIBSC) laboratory and which was obtained by reverse genetics, as described by Nicolson et al., in Vaccine (2005), 23:2943-2952. The viral strains having the H5 or H7 subtype infect especially avian populations, but it is feared that new mutations might occur in the HA protein sequence and that these mutant strains might become infectious to humans and be at the origin of a pandemic flu spreading. Therefore, being able to detect and/or to quantify HAs having the H5 or H7 subtype would be very useful.

The type A and B viral strains recognized by a monoclonal antibody according to the invention are produced using biological material of avian origin. The biological material of avian origin comprises the cells, the tissues, the organs, the exudates or extracts thereof in which the flu virus has multiplied. Usually, the biological material of avian origin comes from hens or chickens. It is in particular cultures of embryonic chicken fibroblasts or of primary cells of chicken embryos.

In particular, the biological material of avian origin containing the flu virus is the allantoic fluid of the hen's egg when the virus is produced on embryonated eggs. This material is used in particular to manufacture flu vaccines. As appropriate, crude material or purified biological material containing purified virus or purified components of said virus is used.

Accordingly:

The flu viruses, the HAs of which are recognized by a monoclonal antibody according to the invention, can be produced on biological material of avian origin.

The immunoenzymatic techniques well known to those skilled in the art and simple to implement, such as direct or indirect ELISA, or the dot-blotting, western blotting or surface plasmon resonance techniques, can normally be used to show that the monoclonal antibody according to the invention recognizes the various HA subtypes (H1, H3, H5 and/or H7 for the type A flu viruses and the HAs originating from the B/Victoria and B/Yagamata groups for the type B flu viruses).

The antigenic structure recognized by a monoclonal antibody according to the invention has been located. The antigen lies on the N-glycosylated part of the various HAs recognized by the monoclonal antibody: treatment of the flu virus HA with N-asparaginase (PNGase) results in a loss of the recognition.

A subject of the invention is therefore:

A monoclonal antibody recognizing an antigenic structure, wherein the antigenic structure is a chain of sugars located on the N-glycosylated part of hemagglutinin.

This results from the observation that the recognition of the antigenic structure by the monoclonal antibody is lost when the flu virus HA is treated with N-asparaginase, which specifically cut the N-glycosidic linkages.

The "N-glycosylated part of the flu hemagglutin" is defined as any chain of sugars bound to the HA amino acid sequence by means of a N-glycosidic linkage that links an asparagine of the HA amino acid sequence to an N acetylglucosamine of the chain of sugars.

The chain of sugars recognized by a monoclonal antibody according to the invention is an oligosaccharide structure containing a small number of sugars that is typically between 3 and 30 sugars, more typically between 3 and 20 sugars, and still more typically between 3 and 10 sugars.

"About" as used herein when referring to a measurable value such as an amount a weight, a temporal duration, and the like, is meant to encompass variations of ±20% or ±10%, more preferably ±5%, even more preferably ±1% with respect to the target measured value.

By means of a monoclonal antibody according to the invention, called Y6F5, the glycosylated antigenic structure recognized has been isolated and characterized by carrying out the following process: the virus produced on embryonated eggs was purified according to conventional methods of those skilled in the art. The HA was subsequently extracted by treating the purified virus with bromelain. The HA was then denatured in such a way that the glycosylated structures became more sensitive to the action of PNGase. To this effect, the protein structure was linearized by treatment with a detergent such as sodium dodecyl sulfate (SDS); the disulfide bridges were then cleaved by treatment with a reducing agent such as dithiothreitol (DTT) followed by alkylation by means of iodoacetamide. The denatured HA was subsequently treated with PNGase: the proteins were precipitated, whereas the supernatant which contains the mixture of glycans was analyzed using the Y6F5 monoclonal antibody attached beforehand to the "sensorchip" of a Biacore 3000. The monoclonal antibody retains only the glycosylated structures that it recognizes. By means of the apparatus used, it was subsequently possible to desorb the antigenic structure which was retained by the monoclonal antibody, using sodium hydroxide. The antigenic structure was subsequently analyzed by mass spectrometry. The MALDI-TOF mass spectrometry analyses showed that it was an oligosaccharide possessing a sulfate group having the following characteristics: it contains galactose, fucose, mannose and N-acetylglucosamine; the sulfate group is attached to the galactose; its molecular weight determined by MALDI-TOF mass spectrometry is about 1240 daltons, accurate to within the areas of uncertainty of the measurements by the apparatus (about +/−10 daltons); the sequence of sugars was subsequently determined and is in the form: fucose-(N-acetylglucosamine)$_2$-(mannose)$_3$-galactose to which is attached a sulfate group (cf. example 2.3). Finally, the inventors identified the definitive structure of the oligosaccharide recognized by the Y6F5 monoclonal antibody as being the sequence depicted in FIG. 3:

Fucose-(N-acetylglucosamine)$_2$-mannose-mannose-galactose-sulfate.
|
mannose

The Y6F5 monoclonal antibody which was used to identify this chemical structure is produced by the Y6F5 hybridoma which was deposited on 10 Jul. 2007 with the Collection Nationale De Cultures de Microorganismes [National Collection of Cultures of Microorganisms] of the Institut Pasteur in Paris (France), 25 rue du Docteur Roux, F-75724 PARIS Cedex 15, under the identification reference Y6F5 and under the registration number CNCM 1-3787.

The monoclonal antibodies according to the invention are usually produced from hybridomas that are obtained by fusing splenocytes of mice hyperimmunized with a solution of purified HA originating from a type A flu virus strain with murine myeloma cells (Sp2/O-Ag14, p3×63Ag8, p3×63-Ag8.653, etc.) according to methods well known to those skilled in the art. The monoclonal antibodies according to the invention generally comprise murine monoclonal antibodies. These monoclonal antibodies are generally tested by ELISA in order to evaluate their ability to recognize the HAs of strains belonging to the H3N2 subtype but also their ability to recognize the HAs of strains belonging to the H1N1 subtype and also the HAs of type B virus strains. Those which recognize both type A virus strains belonging to the H1N1 subtype, type A virus strains belonging to the H3N2 subtype, and type B virus strains can be selected.

It is also verified that they inhibit the hemagglutinating capacity mediated by viral strains belonging to the same subtype as the viral strain which was used to extract the HA used for the immunization of the mice. For example, if the monoclonal antibodies are obtained from mice immunized with a solution of HA originating from a strain having the H3N2 subtype, it is verified that they inhibit the hemagglutinating capacity of H3N2 strains.

It is also verified that they do not recognize the other proteins of the flu virus, in particular the neuraminidase (NA), the M protein and the NP protein.

The characterization of these monoclonal antibodies is completed by studying their behavior with respect to the avian viral strains, in particular as regards their ability to recognize H5N1 or H7N1 viral strains.

In fact, the monoclonal antibodies which recognize both type A strains belonging to the H1N1 subtype, strains belonging to the H3N2 subtype and type B virus strains are preferably selected. Preferably, those which recognize both type B virus strains belonging to the B/Victoria group and to the B/Yagamata group are selected. This is in particular the case of the Y13F9 and Y6F5 antibodies which are described in example 1.

For the characterization of the monoclonal antibodies, methods well known to those skilled in the art, such as ELISA, western blotting, dot-blotting or surface plasmon resonance, are used.

The present invention also encompasses the fragments and derivatives of the monoclonal antibodies of the invention, in particular the Fab, Fab', F(ab)'$_2$ and scFv fragments (Blazar et al, 1997, Journal of Immunology 159: 5821-5833 and Bird et al., 1988, Science 242:423-426), and also the conjugates. The derivatives of the monoclonal antibodies of the invention include, inter alia, the antibodies in a humanized form. The methods for producing monoclonal antibody fragments and also monoclonal antibody derivatives, including in particular antibodies in a humanized form, are well known to those skilled in the art. The humanized forms of nonhuman antibodies, for example murine antibodies, are chimeric antibodies which comprise a minimum sequence derived from a nonhuman immunoglobulin. Most humanized antibodies are human immunoglobulins (receiver antibody) in which residues of a hypervariable region of the receiver are replaced with residues of a hypervariable region of a nonhuman donor species (donor antibody), such as mouse, rat, rabbit or nonhuman primate, having the desired specificity, affinity and capacity. Generally, the hypervariable region comes from the mouse. In certain cases, the residues (FR) of the Fv region of the human immunoglobulin are replaced with corresponding nonhuman residues, most commonly of murine origin. Furthermore, the humanized antibodies can comprise residues which are not found in the receiver antibody or in the donor antibody. These modifications are carried out in order to improve the effectiveness of the antibody. In general, the humanized antibody will comprise at least and preferably two variable domains, in which all or virtually all of the hypervariable loops correspond to a nonhuman immunoglobulin (in general, they correspond to a murine immunoglobulin) and all or virtually all of the FR regions will be those of a human immunoglobulin. The humanized antibodies may optionally also comprise at least a part of a constant region (Fc) of an immunoglobulin, such as a human immunoglobulin (Jones et al., Nature 321: 522-525 (1986); Reichmann et al., Nature 332: 323-329 (1988); and Presta et al., Curr. Op. Struct. Biol. 2: 593-596 (1992)).

The monoclonal antibodies of the invention can be used in an immunoassay for detecting and/or quantifying the HA of a type A or B flu virus in a biological material of avian origin presumed to contain one or more flu virus strains. They can in particular be used in the context of the etiology of a viral infection, or for controlling the content of a flu vaccine. In the context of the diagnosis of an infection, the sample taken is generally a sample from the throat, the trachea or nasal secretions. Use is often made of cloacal or fecal samples when there is a suspicion of avian flu in a poultry farm. Tissue samples can also be taken. The samples are introduced into transporting media (M 199 medium, glycerol-based medium) and then, the flu virus, if it is present in the sample of origin, is generally amplified by inoculating it into embryonated hen eggs. After amplification of the virus, harvesting of the amniotic fluid and centrifugation, the supernatant is removed and tested in an immunoassay by means of a monoclonal antibody according to the invention. The western blotting technique is preferably used when seeking to detect flu virus using the crude allantoic fluid.

In the context of the controls which are carried out on flu vaccines, the amount of HA present in the finished product which is in the form of a purified vaccine is determined or control tests are carried out at the various stages of the manufacture of the vaccine (stage 6, stage 15, stage 21). The biological material may be a purified vaccinal preparation or a preparation which is in the process of being manufactured. The purified vaccinal preparation may be in various forms: whole, attenuated or killed virus, in the form of a splitted virus, of virosomes, or even in a subunit form containing essentially one or more highly purified viral HAs. The vaccine may be in a monovalent form when it is produced from a single virus strain or in a multivalent form when it is produced from several strains (generally two type A virus strains belonging to different subtypes and one type B virus strain). The viruses which are used for the manufacture of the vaccine are generally produced on embryonated eggs and the starting biological material is the infected allantoic fluid. The HA of the type A virus strains which is used for the manufacture of the vaccine is the H1, H3, H5 or H7 subtype.

A subject of the invention is therefore also a method for detecting a flu virus or a flu virus HA in a biological material comprising:

a) contacting said material with a monoclonal antibody, or a fragment or a derivative thereof, according to the invention so as to form antigen/antibody (or fragment or derivative thereof) complexes, and b) detecting the presence of the complexes.

This method is in particular implemented in direct ELISA or dot-blotting techniques or techniques using a Biacore apparatus. The biological material is deposited on a solid support onto which the proteins adsorb, for instance a polystyrene-based, nylon-based or nitrocellulose-based support. After an incubation period, followed by washing, a monoclonal antibody (or fragment or deriviative thereof) according to the invention which is directly or indirectly labeled is added. The monoclonal antibody (or fragment or deriviative thereof) binds specifically to the glycosylated sites of the viral HAs which are adsorbed onto the solid support, thereby forming antigen/antibody (or fragment or deriviative thereof) complexes. The amount of label which is bound to the complexes formed is then measured using conventional techniques of those skilled in the art. The interaction of the antigen with the monoclonal antibody (or fragment or deriviative thereof) can also be evaluated directly during the formation of the complexes by measuring the intensity of the plasmon resonance signal using a Biacore apparatus.

The method for detecting a flu virus in a biological material of avian origin, according to the invention, can also be implemented in the one- or two-dimensional western blotting technique. In this case, the presence of the complexes formed is no longer detected by means of a label or by means of a plasmon resonance signal, as in the previous cases, but through the existence of an electrophoretic band with a molecular weight of approximately 75 KD or of 50 KD (when the material is treated with β-mercaptoethanol) which is characteristic of the HA.

When the biological material of avian origin to be analyzed is enriched in flu viruses or in flu virus components containing HA, and it contains little or no contaminants which can give false-positive results due to the presence of glycosylated contaminants in the material, the direct ELISA or dot-blotting techniques or the Biacore apparatus can be especially used. These techniques are used in particular for detecting or assaying the HA content in a purified flu vaccine which has been obtained using embryonated hen eggs infected with one or more viral strains. A flu vaccine is considered to be purified when the HA content represents at least 30% of the total proteins (w/w).

Western blotting techniques can be especially used when the biological material is nonpurified (such as, for example, infected allantoic fluid) so as to overcome the problem possibly caused by the presence of glycosylated contaminants capable of interacting with a monoclonal antibody according to the invention.

According to another aspect of the invention, the method implemented comprises a prior step according to which the material is brought into contact with a solid support to which is bound a capture agent which specifically recognizes a flu virus structure. The virus, the viral fraction containing HA or the HA is then retained or "captured" specifically on the solid support, whereas the other components of the biological material are eliminated during washes which are carried out after the capture step. The method is then continued as described previously, using a monoclonal antibody (or fragment or deriviative thereof) according to the invention to demonstrate or quantitatively assay the flu virus hemagglutinin(s) present in the biological material.

The capture agent can be bound to the solid support using means known to those skilled in the art, in particular by means of hydrophobic interactions or hydrogen bonds or even by means of covalent bonds.

A monoclonal antibody specific for the protein part of HA is generally used as capture agent, but other capture agents, in particular antibodies directed against the proteins of the viral envelope (for example, antibodies specific for neuraminidase or for the M protein), or even fetuin, could also be used.

Normally, a monoclonal antibody specific for the protein part of flu virus HA is used as capture agent. When the monoclonal antibody has a "strain" specificity, only the HA of a specific viral strain is retained. When the monoclonal antibody has a "subtype" specificity, the HAs of the viral strains which have the same HA subtype are retained on the support. By way of example, mention may be made of the antibodies M322210 (Tebu), MAB825430-2F11-F5-A5 (Chemicon), 9E10 (Nakagawa laboratory) or 7H11 (Nakagawa laboratory), which recognize respectively the H1 and H3 subtypes of HA as far as the first two are concerned, while the last two recognize respectively the HAs of type B viral strains belonging to the Victoria group and the HAs of type B viral strains belonging to the Yagamata group. A monoclonal antibody specific for the protein part of HA is normally used as capture agent, whether for specifically assaying, in biological material, the amount of HA originating from a specific viral strain or the amount of HA originating from one or more strains belonging to the same subtype.

For this reason, a subject of the invention is also, in a specific aspect:

A method for assaying the flu virus hemagglutinin contained in a biological material, which method comprises:

a) contacting the material with a solid support to which is bound a first specific monoclonal antibody (or fragment or deriviative thereof) that recognizes a protein structure of the flu virus hemagglutinin to form antigen/antibody (or fragment or deriviative thereof) complexs;

b) retaining on the solid support the complexes which result from the specific interaction of this monoclonal antibody with the flu virus hemagglutinin contained in the biological material;

c) bringing into contact the complexes retained on the solid support with a second monoclonal antibody (or fragment or deriviative thereof) according to the invention, or a fragment or a derivative thereof, directly or indirectly carrying a label;

d) measuring the amount of label which has bound specifically to the complexes; and e) determining the amount of hemagglutinin contained in the material based on the amount of label measured by comparison with one or more reference reagents.

The second monoclonal antibody (or fragment or deriviative thereof) according to the invention (also referred to as "detection monoclonal antibody") is directly labeled when it has the same isotype and when it originates from the same animal species as the first monoclonal antibody (or capture monoclonal antibody). In the other cases, the second monoclonal antibody can be directly or indirectly labeled. In the case of indirect labeling, the second monoclonal antibody according to the invention can be recognized by means of a directly labeled third antibody specific for the isotype or for the animal species of the second monoclonal antibody.

In a specific embodiment, the assaying method according to the invention can be applied to biological material represented by a vaccinal preparation containing HA originating from one or more different flu virus strains. This vaccinal preparation can be in various forms (provided that it contains HA); it can be in the form of a purified vaccine or of material harvested at the various stages of manufacture of the vaccine, including in particular the infected crude allantoic fluid obtained from infected embryonated hen eggs.

By way of example, the "sandwich-type" immunoenzymatic techniques, or the radioimmunological, immunonephelometric or indirect immunofluorescence techniques well known to those skilled in the art can be applied for implementing this assaying method. Instead of measuring the amount of label, it is possible, in a similar manner, to directly evaluate the interaction of the antigen-antibody complex using the Biacore system.

When the biological material contains little or no glycosylated contaminants that may be recognized by a monoclonal antibody according to the invention, as in the case of purified vaccinal preparations, the capture agent may be represented by a monoclonal antibody according to the invention, such as the Y6F5 monoclonal antibody or the Y13F9 monoclonal antibody. One and the same monoclonal antibody according to the invention may be used both as a capture agent and as a detection monoclonal antibody. Two different antibodies may also be combined, using, for example, the Y13F9 monoclonal antibody as capture monoclonal antibody and the Y6F5 monoclonal antibody as detection monoclonal antibody.

For this reason, in a specific aspect, a subject of the invention is also:

A method for assaying flu virus hemagglutinin contained in a biological material, the method comprising:

a) contacting the material with a solid support to which is bound a first monoclonal antibody (or fragment or deriviative thereof) according to the invention to form antigen/antibody (or fragment or deriviative thereof) complexes;

b) retaining the complexes on the solid support;

c) bringing into contact the complexes retained on the solid support with a second monoclonal antibody (or fragment or deriviative thereof) according to the invention, directly or indirectly carrying a label, wherein the second monoclonal antibody (or fragment or deriviative thereof) is different from or identical to the first monoclonal antibody (or fragment or deriviative thereof, respectively);

d) measuring the amount of label which has bound specifically to the complexes; and e) determining the amount of hemagglutinin contained in the material based on the amount of label measured by comparison with one or more reference reagents.

As indicated above, the second monoclonal antibody (or detection monoclonal antibody) can be directly labeled when it has the same isotype and when it originates from the same animal species as the first monoclonal antibody (or capture monoclonal antibody). In the other cases, the second monoclonal antibody may be directly or indirectly labeled (in this case, the second monoclonal antibody is labeled by means of a directly labeled third antibody which recognizes the isotype or the species specificity of the second monoclonal antibody). In general, in the interests of simplifying the assaying method according to the invention, the second monoclonal antibody is usually directly labeled.

In a specific embodiment, the biological material is represented by a purified vaccinal preparation containing HA originating from one or more flu virus strains. As indicated above, this purified vaccinal preparation may be in various forms provided that it contains flu virus HA. It may in particular contain whole flu virus strains (which may also be inactivated) or splitted flu virus strains, or flu virus strains in the form of virosomes or in the form of a subunit vaccine containing essentially one or more highly purified HAs.

In another aspect, a subject of the invention is:

A method for purifying flu virus or flu virus hemagglutinin from a biological material, comprising:

a) contacting the material with a solid support to which is bound a first monoclonal antibody (or fragment or deriviative thereof) according to the invention to form antigen/antibody antigen/antibody complexes complexes;

b) retaining the complexes on the solid support;

c) releasing the flu virus or the flu virus hemagglutinin from the complexes retained on the solid support; and d) recovering the flu virus or the flu virus hemagglutinin.

The solid support is usually a dextran-based, agarose-based or silica-based chromatographic support. The monoclonal antibody is usually covalently bonded to the chromatographic support using coupling methods well known to those skilled in the art.

The sample to be purified is brought into contact with the immunochromatographic support which selectively retains the flu virus HA or the flu virus. The components not recognized by the monoclonal antibody antigen/antibody complexes according to the invention (contaminants) are not retained on the solid support and are directly eliminated in a chromatographic buffer. The flu virus or the flu virus hemagglutinin is then released from the solid support using specific elution buffers such as glycine buffer at pH=2, or chaotropic agents with a high salt molarity. The chromatographic peak corresponding to the HA or to the flu virus is collected and is generally dialyzed against a physiological buffer. The degree of purity of the preparation can subsequently be increased by combining this purification method with other chromatographic methods, such as excluding chromatography or ion exchange chromatography.

The invention also comprises a pharmaceutical composition comprising one or more antibodies, or fragments or derivatives thereof, according to the invention as a mixture with a pharmaceutically acceptable carrier. The term "pharmaceutically acceptable carrier" is intended to mean the supports and carriers that can be administered to human beings or to an animal, as described, for example, in Remington's Pharmaceutical Sciences 16th edition, Mack Publishing Co.

The invention also comprises a method for preventing or treating flu in a human subject, said method comprising administering to said human subject an effective amount of a pharmaceutical composition as previously described.

The invention therefore also comprises a method of passive immunization against the flu, for therapeutic or prophylactic purposes, which comprises administering to an individual, in particular in humans or in mammals (such as dogs, cats, pigs, horses), or to birds, a therapeutically or prophylactically effective amount of a monoclonal antibody, fragment or derivative of the invention, or combinations thereof. One or more other monoclonal or polyclonal antibodies directed against an antigenic structure located on the protein part of HA or directed against NA may also be associated or combined with one or more monoclonal antibodies according to the invention.

Figure 3:
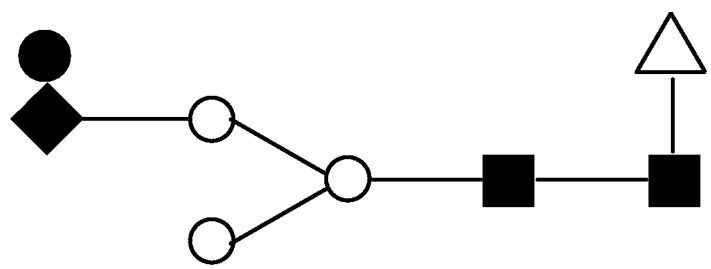
FIG. 3 is a schematic depiction of the structure of the oligosaccharide recognized by the Y6F5 monoclonal antibody.

The invention also comprises the use of a monoclonal antibody according to the invention, in particular the Y6F5 monoclonal antibody, for the isolation and purification of the oligosaccharide which was characterized by the inventors as being, $$\text{Fucose-(N-acetylglucosamine)}_2\text{-mannose-mannose-galactose-sulfate,} \\ | \\ \text{mannose}$$

as depicted in FIG. 3.

Finally, the invention also comprises this oligosaccharide as such and its use for the production of immunosera specific for the type A and B flu virus. The immunogenic potency of this oligosaccharide is reinforced by conjugation of the latter to a carrier molecule or by means of suitable adjuvants.

Therefore, the invention also relates to a pharmaceutical composition comprising a purified oligosaccharide or a conjugated form thereof according to the invention and a method for producing antibodies against type A flu virus or against type B flu virus in an animal, said method comprising administering to said animal an effective amount of said pharmaceutical composition.

The examples which follow illustrate various embodiments of the invention in a nonlimiting manner.

EXAMPLES

Example 1

Obtaining Monoclonal Antibodies According to the Invention 1.1 Production of Monoclonal Antibodies Female BALB/c mice, 6 to 8 weeks old, were immunized according to the following protocol: they received a first intraperitoneal injection of 100 µl of a mixture of purified HA and purified NA, having a hemagglutinating titer of 64,000 units, in the form of an emulsion obtained with an equal volume of complete Freund's adjuvant, followed by two injections 2 weeks apart of the same mixture in the form of an emulsion produced in the presence of incomplete Freund's adjuvant. The mixture of purified HA and purified NA was prepared using the A/Sydney/5/97 (H3N2) IVR 108 strain. The viral strain was produced on embryonated eggs and purified by filtering the infected allantoic fluid through 0.45µ and then performing a sedimentation on a sucrose gradient. The purified viral strain was then treated with triton X100 according to the technique of Gerentes et al. (Journal of Virological methods: 73 (1998) 185-195) so as to obtain the mixture of HA and NA. 3 days after the final injection, the spleen cells were removed and fused with the mouse myeloma cell line p3×63-Ag8.653, according to the technique of Kohler and Milstein. The hybridoma supernatants were screened using ELISA assays in which the "coating" antigen was either the purified virus or the NA which was purified by immunochromatography from the mixture of HA and NA, according to the technique of Gerentes et al. (Journal of Virological methods: 58 (1996) 155-165). The hybridomas which were positive in the ELISA assay using the purified virus as "coating" antigen and which were negative in the ELISA assay using the purified NA as "coating" antigen were subsequently cloned several times and then produced in the form of ascites. The ascites were obtained from mice which had received, beforehand, an injection of Pristane (trade name) followed, a few days apart, by an injection of approximately $10^6$ hybridoma cells. The monoclonal antibodies produced by these hybridomas were subsequently used in the form of ascites fluids or in the form of purified ascites fluids.

The ascites fluids were purified by centrifugation at 10,000 g for 5 minutes at +4° C. The supernatants were subsequently treated with saturated ammonium sulfate (final concentration 40% of the final volume) for 5 min with stirring in order to precipitate the monoclonal antibodies. The precipitates were collected by centrifugation at 3500 g for 15 min. The pellets were taken up in 2 ml of an 8 mM phosphate buffer, pH=7.5 (PBS 1x) without $Ca^{2+}$ and without $Mg^{2+}$, and then dialyzed against 4 liters of 1× PBS without $Ca^{2+}$ and without $Mg^{2+}$ for 2 times 2 h with the PBS being changed after 2 h. The dialyzed monoclonal antibodies were subsequently centrifuged for 10 min at 10,000 g and then assayed by the Bradford method.

For the use in tests for controlling biological samples, in particular for controlling flu vaccines, the most advantageous monoclonal antibodies, such as the Y13F9 monoclonal antibody, were labeled with peroxidase using the Pierce method.

1.2 Study of the Specificity of the Monoclonal Antibodies

The monoclonal antibodies obtained according to the protocol described in paragraph 1.1 and also a certain number of commercially available monoclonal antibodies or monoclonal antibodies originating from the Naoko Nakagawa laboratory (antibodies specific for type B viral strains) were tested for their ability to recognize the hemagglutinins of the A/New Calcdonia/20/99 (H1N1), A/Panama/2007/99 (H3N2) and B/Shandong/7/97 strains (strains of the trivalent vaccine from the year 2003-2004). These viral strains were produced on embryonated eggs and then purified on a sucrose gradient. The amount of HA contained in each purified strain was determined using the official SRD (Single Radial Immunodiffusion) test. The HA content represents at least 30% of the viral proteins.

3 series of ELISA microplates (Dynex® ref: 655071) were coated with one of the 3 purified monovalent strains by introducing into each well 100 µl of a purified monovalent strain containing 1 µg/ml of HA in 0.05M carbonate buffer, pH: 9.6, overnight at +4° C. After the content of the microplates had been suctioned off, the microplates were then saturated for 1 hour at 37° C. with 150 µl/well of a phosphate buffer—0.05% tween 20-1% skimmed milk (saturated buffer). After the content had been suctioned off, successive 2-fold dilutions of each purified monoclonal antibody or monoclonal antibody in the form of ascites fluid were introduced into each well, the first dilution tested being 1/1000. The dilutions were prepared in saturation buffer. Sera of hyperimmunized mice, diluted to 1/10,000, were introduced as positive controls. After incubation for 1.5 hours at 37° C., followed by 4 washes in phosphate buffer—0.05% tween 20 (washing buffer), 100 µl of a peroxidase-labeled sheep anti-mouse Ig conjugate (Amersham NA931), diluted to 1/4,000 in phosphate buffer—0.05% tween 20, were introduced into each well. After a further incubation for 1.5 hours at 37° C., followed by 4 washes, the enzymatic reaction was revealed with a solution of tetramethylbenzidine (TMB); the intensity of the coloration of the wells was measured by spectrophotometry at 450 and at 600 nm. For each monoclonal antibody tested, a titer which is the inverse of the dilution of the antibody (expressed as $\log_{10}$) which gave an optical density (O.D) of 1 at 450 nm was thus determined. A titer less than or equal to 2.7, symbolized in table 1 in the form (≤) means that the monoclonal antibody does not recognize the HA of the purified monovalent strain. 2 monoclonal antibodies were identified, produced by the Y13F9 and Y6F5 hybridomas, which were obtained according to the protocol of example 1, which recognize the HAs of the 3 purified strains: A/New Calcdonia/20/99 (H1N1), A/Panama/2007/99 (H3N2) and B/Shandong/7/97 (titer >2.7 in the 3 ELISA assays). On the other hand, none of the commercial antibodies (1351, 48079, M322210, 58CE8-1-5, 58AB7-19-18, 621D5-11, 30-2F11-F7-A5, BGN/5G8, C102, 3B3, 4H7) or those of the Naoko Nakagawa laboratory (1H12, 2H12, 5B12, 9E10, 10B8) (which obtained a battery of monoclonal antibodies against the type B viral strains (Journal of Virological methods 79: 113-120 (1999); Journal of Medical Virology 65:745-750 (2001); Journal of General Virology 82: 2169-2172)), recognize the HAs of the 3 strains. The 30-2F11-F7-A5 monoclonal antibody recognizes the HAs of the A/New Calcdonia/20/99 (H1N1) and A/Panama/2007/99 (H3N2) strains. The other antibodies recognize just one of the 3 strains tested (cf. table 1).

TABLE 1

Recognition of the A/NC/20/99 (H1N1), A/Panama/2007/99 (H3N2) and B/Shangdong/7/97 strains by various monoclonal antibodies directed against flu virus HA.

| Hybridoma name | Isotype | Specificity "of origin" | A/New Caledonia/20/99 (H1N1) | A/Panama/ 2007/99 (H3N2) | B/ Shandong/ 7/97 (B) |
|---|---|---|---|---|---|
| Y13F9 | IgM | A/Sydney/5/97 (H3N2) | 5.25* | 5.28 | 5.3 |
| Y6F5 | IgM | A/Sydney/5/97 (H3N2) | 3.9 | 3.97 | 4.0 |

TABLE 1-continued

Recognition of the A/NC/20/99 (H1N1), A/Panama/2007/99 (H3N2) and B/Shangdong/7/97 strains by various monoclonal antibodies directed against flu virus HA.

| Hybridoma name | Isotype | Specificity "of origin" | A/New Caledonia/20/99 (H1N1) | A/Panama/ 2007/99 (H3N2) | B/ Shandong/ 7/97 (B) |
|---|---|---|---|---|---|
| 1351 | IgG1 | H1N1 | 3.6 | ≤ | ≤ |
| 48079 | IgG1 | H1N1 | 5.65 | ≤ | |
| M322210 | IgG1 | H1N1 | 5.80 | ≤ | ≤ |
| 58CE8-1-5 | | A/Taiwan/1/86 (H1N1) | ≤ | | |
| 58AB7-19-18 | IgG1 | H1N1 | ≤ | 3.0 | ≤ |
| 62ID5-11 | | A/Shang./11/97 (H3N2) | | ≤ | |
| 30-2F11-F7-A5 | IgG2a | H3N2 | 2.85 | 5.6 | ≤ |
| BGN/5G8 | | B/Panama/45/90 | ≤ | ≤ | ≤ |
| C102 | IgG1 | H1N1 | 5.8 | ≤ | ≤ |
| 3B3 | | H1N1 | 5.25 | ≤ | NS |
| 4H7 | IgG1 | B/Panama/45/90 | ≤ | ≤ | ≤ |
| 1H12 | IgG1 | B/Nagasaki/1/87 | ≤ | ≤ | 5.1 |
| 2H12 | IgG3 | B/Nagasaki/1/87 | ≤ | ≤ | 4.8 |
| 5B12 | | B/Nagasaki/1/87 | ≤ | ≤ | 3.1 |
| 9E1O | IgG1 | B/Nagasaki/1/87 | ≤ | ≤ | 6.1 |
| 10B8 | IgG2a | B/Nagasaki/1/87 | ≤ | ≤ | >6.1 |

*ELISA titer
NS: not specific

The Y13F9 and Y6F5 monoclonal antibodies were also tested for their ability to recognize other flu virus strains, in particular the A/Taiwan/1/86xX31 (H1N1), A/Chile/1/83X83 (H1N1), A/Wisconsin/67/2005 (H3N2), A/New York/55/2004 (H3N2), A/Wyoming/03/2003 (H3N2), A/Hong Kong/1/68 (H3N2), A/Mississippi/1/85X87 (H3N2), A/Sichuan/2/87 (H3N2), A/Leningrad/360/86 (H3N2), A/Shanghai/11/87X99, B/Malaysia/2506/04, B/Jiangsu/10/2003, B/Brisbane/32/02, B/Yagamata/16/88 and B/Beijing/1/87 strains. All these strains were produced on embryonated eggs and purified, and were in the form of purified viruses, or of splitted viruses when the purified virus had undergone a treatment with tween-ether or with triton. In certain cases, the strains tested were in the form of a monovalent vaccine or of a mixture of monovalent vaccines. An indirect sandwich ELISA technique, in which the HA of the virus strains tested is sandwiched between the Y13F9 or Y6F5 monoclonal antibody which was used as capture monoclonal antibody and the Y13F9 monoclonal antibody directly labeled with peroxidase, which was used as the detection monoclonal antibody, was used. To implement the technique, the ELISA plates were coated with 100 μl of a solution of purified monoclonal antibody (used as capture monoclonal antibody) at a concentration of approximately 2 μg/ml in carbonate buffer, pH=9.6, overnight at +4° C., followed by a step for saturation of the plates as above. 100 μl of a sample of the strain to be tested were then deposited, successive dilutions of the sample being performed in a saturation buffer, and then the microplates were left to stand for 1.5 hours at 37° C. After washing of the plates, 100 μl of a solution of a detection monoclonal antibody (monoclonal antibody Y13F9 directly labeled with peroxidase), at the concentration of 0.1 μg/ml in saturation buffer, were deposited. After a further incubation for 1.5 hours at 37° C., followed by washes, the detection step and step for measuring the intensity of the reaction were carried out as above. The results revealed that all the H1N1 and H3N2 strains and the B virus strains tested were recognized both by the Y6F5 monoclonal antibody and the Y13F9 monoclonal antibody. These two monoclonal antibodies also inhibited the hemagglutinating activity of the A/Beijing/32/92 (H3N2), A/Shangdong/9/93 (H3N2), A/Johannesburg/33/94, (H3N2), A/Nanchang/933/95 (H3N2) and A/Sydney/5/97(H3N2) virus strains. Finally, the A/Vietnam/1194/04 strain, which is an H5N1-type avian strain, is recognized by the Y13F9 monoclonal antibody.

These results clearly prove that the Y6F5 and Y13F9 monoclonal antibodies recognize both the H3 and H1 hemagglutinins of type A flu viruses, since numerous H3N2 and H1N1 strains are recognized, but also the hemagglutinins of type B flu viruses, since numerous type B flu virus strains belonging both to the B/Yagamata group and to the B/Victoria group are recognized. The Y13F9 monoclonal antibody also recognizes hemagglutinin H5.

1.3 Use of the Monoclonal Antibodies for Controlling Flu Vaccines

We used two indirect (sandwich) ELISA methods.

In the first method, the capture antibody was a "subtype"-specific monoclonal antibody or a type B virus-specific monoclonal antibody, the detection monoclonal antibody being the Y13F9 monoclonal antibody labeled with peroxidase. This "subtype"-specific or type B virus-specific ELISA made it possible to assay the HA content of each of the strains present in a trivalent vaccine. It in fact contained two type A virus strains belonging to different subtypes and one type B virus strain. The amount of HA of each of the vaccinal strains contained in the trivalent vaccine was assayed by carrying out 3 different "strain"-specific ELISAs which differed only in terms of the capture antibody. The total amount of HA contained in the trivalent vaccine was determined by adding the three amounts.

In the second method, one and the same monoclonal antibody according to the invention, used both as capture monoclonal antibody and as detection monoclonal antibody, was used. The Y13F9 monoclonal antibody was used as capture monoclonal antibody and the Y13F9 monoclonal antibody labeled with peroxidase was used as the detection monoclonal antibody. The total amount of HA contained in the trivalent vaccine was determined by carrying out a single ELISA, but, in this case, the amount of HA which "was down to" each of the strains could not be assayed. This method of assaying is considered to be "polyspecific" since the amount of HA contained in flu vaccines from different years can be controlled.

These two methods were used in the context of controls carried out on vaccine from the year 2003-2004, which contained the A/New Calcdonia/20/99 (H1N1), A/Panama/2007/99 (H3N2) and B/Shandong/7/97 strains. The vaccine was controlled at various stages of its manufacture: at the beginning of its manufacture, i.e., at the stage where the vaccine was represented by the infected crude allantoic fluid (stage 6), at the stage where the vaccine was in the form of concentrated and purified whole virus (stage 15), and at the stage where the vaccine was in the form of a trivalent vaccine (vaxigrip) (vaccine containing the 3 strains of viruses that had been purified and splitted under the action of detergent). In the context of these controls, the reference antigens provided by the NISBC, which were solutions of semi-purified viruses originating from the A/New Calcdonia/20/99 strain (batch 01/614), from the A/Panama/2007/99 strain (batch 02/100) or from the B/Shandong/7/97 strain (batch 02/108) and which had theoretical titers of 65, 53 and 55 µg/ml of HA according to the SRD reference method, were also used. Controls were also performed on the purified HA extracted from each of the 3 concentrated and purified virus strains (stage 15) by treatment with bromelain followed by exclusion chromatography (purified HA). The protocol followed for the extraction and the purification of the HA was that described in paragraph 2.1.

To carry out the 3 specific ELISAs of the first method, a purified preparation of M322210 monoclonal antibody (Fitzgerald-ref 10I50) was used as capture monoclonal antibody to assay the HA content of the A/NC/20/99 strain (H1N1), a purified preparation of MAB825430-2F11-F7-A5 monoclonal antibody (Chemicon-ref mab8254) was used as capture monoclonal antibody to assay the HA content of the A/Panama/2007/99 strain (H3N2) and a preparation of 9E10 monoclonal antibody was used for the B/Shangdong/7/97 strain. They were diluted in 0.05M carbonate/bicarbonate buffer, pH 9.6, and then deposited, at 1/1000th, at the bottom of the wells of a 96-well plate (Dynex) at a rate of 100 µl per well. After an overnight period at 4° C., the plate was emptied and then saturated with 150 µl per well of phosphate-tween 20 (0.05%) buffer containing 1% of skimmed milk. After incubation for 1 h 30 at 37° C., the plate was again emptied, and then 100 µl of the sample to be assayed, treated or not treated with zwittergent, were deposited per well. The samples to be assayed were conserved at −80° C. and sonicated after thawing before use. Moreover, if the samples to be controlled contained non splitted virus (antigens of the NIBSC, stage 6 or stage 15), they were brought into contact, beforehand, for 30 min at laboratory temperature with stirring, with a solution of 10% (w/v) of zwittergent at a rate of 9 volumes of sample per 1 volume of the zwittergent solution. If the concentration of the sample was known by SRD, it was diluted (in the saturation buffer), so as to deposit, in the 1st well, 1 µg/ml of HA, and then the sample was subsequently serially diluted 2-fold over 12 cupules. This is what was done, for example, for the reference and the control. If the concentration of the sample to be titered was unknown, it was deposited pure in the 1st well and then serially diluted 2-fold over 12 wells. The plate was then incubated for 1 h 30 at 37° C., emptied, washed 4 times in phosphate-tween 20 (0.05%) buffer, and then 100 µl of Y13F9 monoclonal antibody conjugated to peroxidase and diluted to 1/10,000th in the saturation buffer were added to each well. The plate was incubated again for 1 h 30 min at 37° C., then its content was emptied out and it was washed 4 times, and the sandwich was revealed with 100 µl of 3,3',5,5'-tetramethylbenzidine (TMB, Tebu Bio). After 20 min, the reaction was stopped with 100 µl of 1N HCl (Prolabo). The plates were read at 450-650 nm (Molecular Devices Versa Max).

A reference and a control, which corresponded to a monovalent vaccine (i.e., a strain of purified virus splitted under the action of detergent), assayed via SRD were deposited, for each strain, onto each plate. A 4-parameter curve was thus established, which made it possible to quantify the HA in the samples to be controlled (Soft Max Pro software).

By using this ELISA assaying method, there is no longer any need to use the NISBC reagents as reference antigens. It is possible to use, as reference, a strain-specific monovalent assayed by ELISA against purified HA, itself assayed by the Bradford method. In this case, it is no longer necessary to wait for the SRD assay of the monovalent before using it as reference.

The amount of HA of each sample was measured in µg/ml using the Soft Max Pro software between the optical density (OD) values of 0.2 and 2.0, then calculated from the curve obtained with the reference monovalent.

The operating protocol used for the polyspecific ELISA was the same as that which has been described, with the following particularities. The capture monoclonal antibody was a purified solution of Y13F9 monoclonal antibody used at a concentration of 2 µg/ml in carbonate buffer, pH=9.6. The samples to be controlled, which contained non splitted virus (NIBSC antigens, or stage 15), were not pretreated with zwittergent.

The specific ELISA titers were compared with the SRD titers when the latter were available or with the Bradford assay when purified HA was involved. The results obtained using the strain-specific ELISA methods are given in table 2. The results obtained using the polyspecific ELISA method are given in table 3.

TABLE 2

Assaying of the HA of the A/NC/20/99 (H1N1) strain, of the HA of the A/Panama/2007/99 (H3N2) strain and of the HA of the B/Shangdong/7/97 strain in various flu samples (specific ELISA)

| Strain | Nature of the sample | ELISA titer (µg/ml of HA) | SRD or Bradford titer (µg/ml of HA) |
|---|---|---|---|
| A/NC/20/99 (H1N1) | NIBSC* Ag | 12.46 | 65 (SRD) |
| | Stage 6* | 2.6 ± 0.31 | NA |
| | Stage 15* | 104.46 | NA |
| | Purified HA | 1025.49 | 747 (Bradford) |
| | Vaxigrip | 25.31 ± 13.1 | 30 (SRD) |
| A/Panama/2007/99 (H3N2) | NIBSC* Ag | 14.52 | 53 (SRD) |
| | Stage 6* | 2.78 ± 1.47 | NA |
| | Stage 15* | 300.1 | NA |
| | Purified HA | 108.34 | 318 (Bradford) |
| | Vaxigrip | 48.53 ± 10.38 | 30 (SRD) |
| B/Shangdong/7/97 | NIBSC* Ag | 26.24 | 55 (SRD) |
| | Stage 6* | 10.07 ± 5.32 | NA |
| | Stage 15* | 114.01 | NA |
| | Purified HA | 1289.52 | 2032 (Bradford) |
| | Vaxigrip | 60.6 ± 16.35 | 30 (SRD) |

*indicates that the sample was treated with zwittergent
NA: not applicable

The samples which were titered 2 or even 3 times have ELISA titers which then correspond to mean values±the standard deviation. The samples which were titered only once have just one indicated value. The SRD titer can vary by approximately 20%. The detection limit is of the order of 1 ng/ml.

TABLE 3

Assaying of the HA of the A/NC/20/99 (H1N1) strain, of the HA of the A/Panama/2007/99 (H3N2) strain and of the HA of the B/Shangdong/7/97 strain in various flu samples (polyspecific ELISA)

| Strain | Nature of the antigen | ELISA titer (µg/ml of HA) | SRD titer or Bradford titer (µg/ml of HA) |
|---|---|---|---|
| A/NC/20/99 (H1N1) | NIBSC Ag | 65.92 ± 31.57 | 65 (SRD) |
| | Stage 15 | 415.33 ± 51.83 | NA |
| | Purified HA | 628.34 ± 60.14 | 747 (Bradford) |
| | Vaxigrip | 65.42 ± 5.04* | 90 (SRD) |
| A/Panama/ 2007/99 (H3N2) | NIBSC Ag | 36.58 ± 18.32 | 53 (SRD) |
| | Stage 15 | 158.20 | NA |
| | Purified HA | 238.22 ± 11.89 | 318 (Bradford) |
| | Vaxigrip | 108.94 ± 23.13* | 90 (SRD) |
| B/ Shangdong/ 7/97 | NIBSC Ag | 79.93 ± 22.67 | 55 (SRD) |
| | Stage 15 | 594.88 ± 114.78 | NA |
| | Purified HA | 1442.77 ± 44.80 | 2082 (Bradford) |
| | Vaxigrip | 214.15 ± 34.73* | 90 (SRD) |

NA: not applicable
*the values obtained are not equivalent since the references used were different in the 3 assays. In the first assay, the reference was the purified and split monovalent A/NC/20/99 strain, in the second assay, the reference was the purified and splitted monovalent A/Panama/ 2007/99 strain and in the third assay, the reference was the purified and split monovalent B/Shangdong/7/97 strain.

The samples which were titered 2 or even 3 times have ELISA titers which then correspond to mean values±standard deviation. The samples which were titered only once have just one indicated value. The SRD titer can vary by approximately 20%. The detection limit is of the order of 1 ng/ml.

In general, good correspondence is observed between the titers obtained with the SRD method or the Bradford method and the titers obtained with the specific ELISAs or with the polyspecific ELISA method. With respect to the reference antigens of the NISBC, it is noted that there is better correspondence between the ELISA titers and the SRD titers when the polyspecific ELISA method is used. With respect to the highly purified HA, irrespective of the origin of the strain, it is also noted that there is better correspondence between the ELISA titers and the titers obtained by the Bradford method when the polyspecific ELISA method is used.

The specific ELISAs have the advantage of being able to quantify each strain as a mixture in a trivalent, and of searching for possible heterologous contaminations, but it is necessary to be able to have monoclonal capture antibodies specific for the vaccinal strains of the year.

The "polyspecific" ELISA has the advantage of being able to quantify any purified flu virus strain while escaping the vagaries of recurrent supply of specific antibodies.

The two methods, in particular that which requires the use of specific ELISAs, make it possible to envision production controls on line, and especially the high-risk formulation of the Vaxigrip trivalent vaccine from bulk quantities of each monovalent; independently of the availability of the NIBSC reagents.

Example 2

Characterization of the Antigenic Structure Recognized by the Monoclonal Antibodies According to the Invention 2.1: The Antigenic Structure Recognized by the Monoclonal Antibody is a Glycosylated Motif The A/New Calcdonia/20/99 (H1N1) strain, purified according to the operating protocol of example 1, was inactivated overnight at +4° C. with a solution of β-propiolactone diluted to 1/1000th, and then ultracentrifuged. The viral pellet was then subjected to a double treatment with bromelain by adding 55 µg of bromelain per mg of purified virus in suspension in PBS, and then by adding 8 µl of β-mercaptoethanol per ml of mixture overnight at +4° C. The HA of the viral envelope was thus extracted. The supernatant was then subjected to exclusion chromatography on superose 6 gel (Pharmacia) in an 8 mM PBS buffer in order to isolate and collect the eluate containing the HA.

A part was then treated with PNGase F by adding, to the solution of HA (pH=7.5), 1.3 units of PNGase F (Calbiochem ref: 362185.) per mg of HA. PNGase F is an endoglycosidase which cleaves N-glycans at asparagine sites. After treatment for 2 hours at 37° C., a deglycosylated HA was obtained. The other part was not treated with PNGase. The HA samples treated or not treated with PNGase F were controlled by western blotting by means of the Y6F5 and Y13F9 antibodies used at the concentration of 1 µg/ml and of an alkaline phosphatase-coupled anti-mouse conjugate (Zymed ref: 61-6422) diluted to 1/1000th. The results showed that a band of 55 KD existed when the sample was not treated with PNGase F. On the other hand, the band has a lower mass when the sample was pretreated with PNGase F.

2.2: Characterization of the Glycosylated Motif 2.2.1: Treatment of the HA Originating from the B/Jiangsu Virus Strain and Extraction of Glycans The Y6F5 monoclonal monoclonal antibody and the B/Jiangsu virus strain purified by sucrose gradient sedimentation were selected for this characterization.

The extraction of the HA was carried out according to the same protocol as that described in the previous paragraph. The residual virus was removed by ultracentrifugation for 1 hour at 100,000 g at 4° C. The HA was in the ultracentrifugation supernatant.

The HA was then denatured in the presence of sodium dodecyl sulfate (SDS) by adding 1 mg/ml of sodium dodecyl sulfate to a solution of 2.2 mg/ml of HA. After 5 minutes, dithiothreitol (DTT) was added such that the final concentration of DTT in the mixture was 5 mM. After incubation at 60° C. for 15 minutes, iodoacetamide was added such that the final concentration of iodoacetamide in the mixture was 10 mM. After a further incubation for 20 minutes in the dark at laboratory temperature, the mixture was finally dialyzed against a PBS buffer.

The glycoprotein was then in a linear form and the glycans were more exposed for enzymatic cleavage with PNGase F.

The denatured HA, at a concentration of approximately 1 mg/ml was then treated with PNGase F (ref: Calbiochem ref: 362185) for 16 h at a rate of 0.4 units/mg in a 50 mM phosphate buffer, pH=7.5. During the period of the enzymatic treatment, its enzymatic activity with respect to HA was controlled by carrying out an electrophoresis on polyacrylamide gel in the presence of SDS. The endoglycosidase activity of the PNGase F results in a decrease in mass of the HA, which is characterized on a polyacrylamide gel by the existence of a band of lower mass.

After the action of the enzyme, the proteins were precipitated by treatment with 10% trichloracetic acid. The supernatant which contained a mixture of glycans was finally collected after centrifugation for 15 min at 10,000 g. In parallel, the same treatments were carried out on an aliquote of purified HA originating from the purified B/Jiangsu virus, with the exception of the PNGase F treatment. This sample was used as a negative control for the subsequent experiments.

2.2.2: Purification of Glycans Using Biacore 3000

The Y6F5 monoclonal antibody at a concentration of 250 µg/ml in 10 mM acetate buffer, pH=4.5, was covalently bound to the sensorchip of the Biacore 3000 using the supplier's instructions. The HA sample which was treated with PNGase F and also the negative control, which was not treated, were then injected into the apparatus.

The signal of the monoclonal antibody-captured glycans which is observed is enormous (approximately 1000 RU) although the amount of material used is very small (a few μg). No signal was observed with the sample which serves as a negative control.

The glycans retained by the Y6F5 monoclonal antibody were then desorbed from the sensorchip by injecting a few μl of a 5 mM sodium hydroxide solution. 2 μl of a solution of glycans were recovered at the outlet of the apparatus. The experiment was carried out twice in order to have a sufficient volume.

1 ul of trifluoroacetic acid (TFA) was then added to the solution of purified glycans before analyzing the sample by mass spectrometry.

2.2.3: Characterization of the Glycosylated Motif

The analysis was carried out on a MALDI T of apparatus (Autoflex II Bruker). This type of apparatus was chosen because of the small amount of analyte available. The ions were detected in the negative reflectron mode.

The preparation of the matrix and of the analyte and its deposition were carried out as follows: the matrix used was dihydroxybenzoic acid (DHB). The preparation of the matrix was carried out by preparing a saturating solution of matrix in acetone and then the supernatant was subsequently diluted by adding a volume of water. One μl of this solution of matrix was then mixed with 1 μl of analyte containing the glycans. 0.5 μl of this mixture was then deposited onto the stainless steel MALDI plate at two different places.

The identification of the oside structure was carried out by subtraction of the spectra obtained between the sample treated with PNGase F and the sample not treated with PNGase (negative control).

The comparative analysis of the two spectra made it possible to detect an ion at the mass of 1240 Da (cf. FIG. 1). We then calculated the number of sugars involved in this structure on the basis of the structures of the flu glycans described in particular by W Keil et al. (Virology, 133, 77-91 (1984)) and more recently by S.Y. Mir-Shekari et al. (Journal of biological Chemistry, 272, 4027-4036 (1997)). The structure of the basic oligosaccharide sequence: $(glucose)_3$-$(mannose)_9$-$(N$-acetylglucosamine$)_2$, in its three-antenna form, which is transferred by means of dolichol phosphate and from which the transformation processes are carried out, which processes are generally reflected by the loss of glucose residues, by the loss of mannose residues to varying degrees and by the introduction of new sugar residues, which are N-acetylglucosamine, galactose and fucose, which graft onto the modified basic structures, was used as a foundation to determine the structure of the oligosaccharide recognized by the Y6F5 monoclonal antibody on the basis of its molecular weight of 1240 daltons. By studying all the possible combinations of sugar residues we came to the conclusion that there was none which made it possible to determine the mass of our ion. It was therefore considered that a nonsugar residue may also be present on the glycoside motif recognized by the Y6F5 monoclonal antibody, in particular a sulfate group.

In order to support this hypothesis, the solution of purified glycans, recovered at the outlet of the apparatus, was treated with a volume of a 1M aqueous ammonia solution at 60° C. for 1 hour. The purpose of this treatment was to remove the sulfate groups possibly attached to the sugar residues. The example obtained was then treated and analyzed in the same manner.

As shown in FIG. 1 (top spectrum), we note a loss of mass of 80 Da characteristic of the loss of a sulfate group. This therefore confirms the existence of a sulfate group on the glycosylated motif recognized by the Y6F5 monoclonal antibody. The spectrum of the sample of purified glycans not treated with aqueous ammonia shows two peaks of interest (at 1240 and at approximately 1160) (cf. bottom spectrum in FIG. 1); this is due to the lability of the sulfate group during the ionization of the analyte.

It is also observed that the two spectra are not of equivalent quality. This is explained by the fact that, in addition to the dilution brought about during the desulfation experiment, the latter introduced ammonium groups which substituted for the salts already present. The combination of these two phenomena means that the molecular ion is predominantly observed and the adducts are observed to a much lesser degree.

On the basis of the MW of the glycan motif isolated by immunoaffinity by means of the Y6F5 monoclonal antibody and the desulfation experiments, it was deduced therefrom that the glycan motif contains 7 sugars. It comprises the motif: $(N$-acetylglucosamine$)_2$-$(mannose)_3$ of the basic structure, onto which two additional sugars are grafted. According to the MWs of the sugar residues which bind to the modified basic structure, i.e., N-acetylglucosamine, galactose and/or fucose, the only possibility which is compatible with the MW of the isolated glycan is that a galactose and a fucose graft to the $(N$-acetylglucosamine$)_2$-$(mannose)_3$ motif. In this case, the MW of all these 7 sugars, which is 1160 Da, corresponds to the MW of the desulfated glycan motif determined by mass spectrometry. The fucose is linked to the N-acetylglucosamine, while the galactose is linked to a mannose residue as is conventionally observed. The sequence of sugars of the glycosylated motif recognized by the Y6F5 monoclonal antibody is therefore: fucose-$(N$-acetylglucosamine$)_2$-$(mannose)_3$-galactose. The sulfate group is linked to a galactose since the cells in which the flu virus reproduces contain an enzyme for galactose sulfation (galactose sulfatase).

In fact, the structure of the glycan motif recognized by the Y6F5 monoclonal antibody is of the form depicted in FIG. 3.

What is claimed is:

1. A flu virus hemagglutinin-specific monoclonal antibody, or an antigen-binding fragment thereof, produced by the Y6F5 hybridoma deposited with the Collection Nationale De Cultures de Microorganismes of the Institut Pasteur in Paris (France) under registration number CNCM 1-3787.

2. The monoclonal antibody of claim 1, wherein the antibody binds to type B flu viruses belonging to the B/Victoria group.

3. The monoclonal antibody of claim 1, wherein the antibody binds to type B flu viruses belonging to the B/Yagamata group.

4. The monoclonal antibody of claim 3, wherein the flu viruses are produced on biological material of avian origin.

5. The monoclonal antibody of claim 1 that is produced by the Y6F5 hybridoma, in humanized form.

6. An antigen-binding fragment of the antibody of claim 1 wherein the fragment is Fab, Fab', F(ab)'$_2$, or scFv.

7. A pharmaceutical composition comprising the monoclonal antibody or antigen binding fragment of claim 1, wherein the antigen binding fragment is selected from the group consisting of a Fab, Fab', F(ab)'$_2$ or scFv.

8. A method for producing the antibody or antigen binding fragment of claim 1, comprising culturing the Y6F5 hybridoma deposited with the Collection Nationale De Cultures de Microorganismes of the Institut Pasteur in Paris (France) under registration number CNCM 1-3787 and isolating the secreted monoclonal antibody.

9. A method for detecting a flu virus or a flu virus hemagglutinin in a biological material, comprising:
   a) contacting said material with the monoclonal antibody or antigen binding fragment of claim 1 to form antigen/antibody complexes; and
   b) detecting the presence of antigen/antibody complexes.

10. A method for assaying for flu virus hemagglutinin contained in a biological material comprising:
   a) contacting a biological material with a solid support to which is bound the monoclonal antibody or antigen binding fragment of claim 1 to form an antigen/antibody complex on the solid support;
   b) bringing the complexes of step a) into contact with a second specific monoclonal antibody that recognizes a protein structure of the flu virus hemagglutinin, directly or indirectly carrying a label;
   c) measuring the amount of label which has bound specifically to the complexes; and
   d) determining the amount of hemagglutinin contained in the material based on the amount of label measured by comparison with one or more reference reagents.

11. The method of claim 10 where in step b) the monoclonal antibody or antigen binding fragment of claim 1 is used, and in step a) a different monoclonal antibody that recognizes a protein structure of the flu virus hemagglutinin is used.

12. The method of claim 10, wherein the biological material is a vaccinal preparation containing hemagglutinin originating from one or more flu virus strains.

13. A method for purifying a flu virus or a flu virus hemagglutinin from a biological material of avian origin, comprising:
   a) contacting the material with a solid support to which is bound the monoclonal antibody or antigen binding fragment of claim 1 to form antigen/antibody complexes;
   b) releasing the flu virus or the flu virus hemagglutinin from the complexes; and
   c) recovering the flu virus or the flu virus hemagglutinin.

14. The monoclonal antibody of claim 2, wherein the flu viruses are produced on biological material of avian origin.

* * * * *